US00PP09104P

United States Patent [19]

Cadic

[11] Patent Number: Plant 9,104

[45] Date of Patent: Apr. 11, 1995

[54] FORSYTHIA PLANT — COURTASOL VARIETY

[75] Inventor: M. Alain Cadic, Beaucouze cedex, France

[73] Assignee: Agri Obtentions S.A., Guyancourt cedex, France

[21] Appl. No.: 226,473

[22] Filed: Apr. 11, 1994

[51] Int. Cl.[6] ..... A01H 5/00
[52] U.S. Cl. ..... Plt./54.1
[58] Field of Search ..... Plt. 54.1

*Primary Examiner*—James R. Feyrer
*Attorney, Agent, or Firm*—Burns, Doane, Swecker & Mathis

[57] ABSTRACT

A new and distinct variety of Forsythia plant named Courtasol is provided. The new variety was discovered among the open-pollination progeny growing in a cultivated area of a fertile mutant that was created by subjecting *Forsythia×intermedia* Spring Glory to gamma rays. Unlike its parent the new variety exhibits a distinctive low-growing, compact and spreading growth habit. Short internode lengths make possible a dense and abundant display of bright yellow blossoms in the springtime. A mature plant commonly assumes a height of approximately 0.5 meter and a width of approximately 1.2 meter. The new variety is particularly suited for growing as attractive ornamentation in the landscape.

2 Drawing Sheets

SUMMARY OF THE INVENTION

The new variety was discovered and selected by me as a chance seedling obtained among the open-pollination progeny of a fertile mutant of the Spring Glory variety of *Forsynthia×intermedia* that was induced by treating buds with an acute dose (50 Gy) of gamma rays and growing in a container at Beaucouze, France. The Spring Glory variety is non-patented in the United States. The pollen parent was unknown since open pollination was employed.

I was attracted to a single plant that exhibited a distinctive growth habit unlike that of the Spring Glory variety growing nearby. Had I not discovered and preserved the plant of the new variety of the present invention it would have been lost to mankind.

It was found that the new variety:

(a) exhibits a distinctive low-growing, compact and spreading growth habit, and
(b) forms a dense and abundant display of attractive bright yellow flowers that is influenced by the short internode length.

The plant is particularly suited for growing as attractive ornamentation in the landscape. The main branches commonly extend upwards at angles of approximately 45° and tend to bend downwards as they elongate. The secondary foliage tends to be upright, and contributes to the formation of compact and dense shrub. The short internodes serve to make possible the substantially complete coverage of the plant with attractive bright yellow blossoms during the Spring. A mature plant of the new variety commonly assumes a height of only approximately 0.5 meter and a width of approximately 1.2 meter.

No seed set has been observed on plants of the new variety to date.

The new variety has been found to readily undergo asexual propagation by softwood cuttings. More specifically, asexual propagation of the new variety carried out on a large scale in France, and at West Grove, Pa., U.S.A., has demonstrated that the unique combination of characteristics of the new variety has been well established and is well transmitted to successive generations. The resulting plants consistently exhibit all of the traits of the new variety.

The new variety has been named the Courtasol variety and is being marketed under the Gold Tide trademark.

BRIEF DESCRIPTION OF THE PHOTOGRAPHS

The accompanying photographs show typical specimens of the new variety of Forsythia plant as depicted in color as true as is reasonably possible to make the same in color illustrations of this character. The plants illustrated were produced by softwood cuttings and were grown at St. Barthelemy d'Anjou, France.

DETAILED DESCRIPTION

Figure 1:
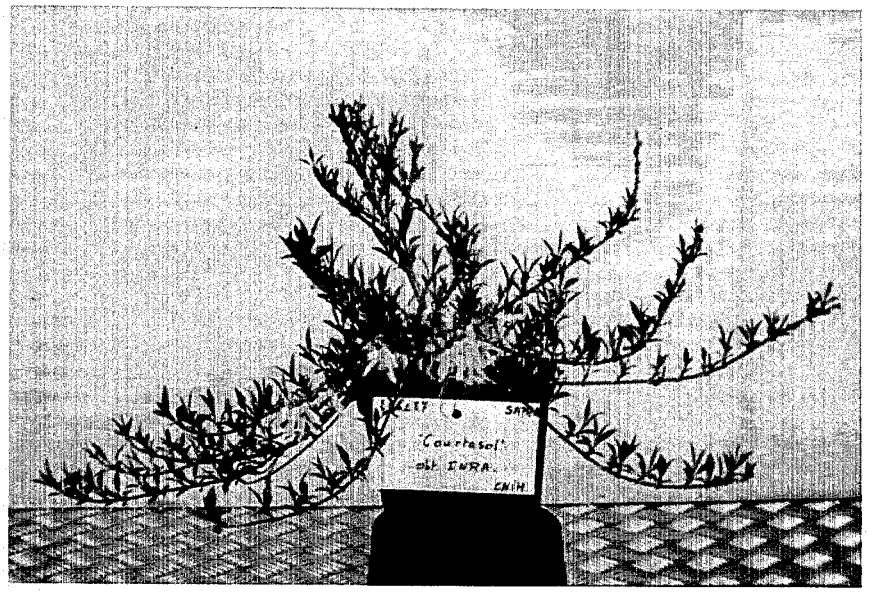
FIG. 1 illustrates a two year-old plant while grown in a container at the conclusion of the flowering season wherein the upwardly extending leaves have begun to form. The distinctive spreading growth habit and the short internode lengths are apparent.
Figure 2:
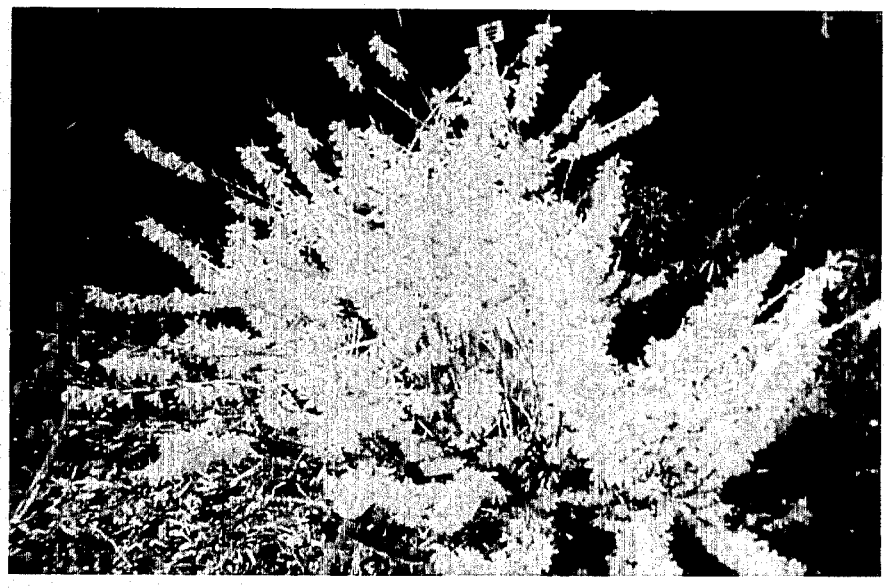
FIG. 2 illustrates a young plant while growing outside in the landscape wherein the profusion of attractive bright yellow flowers is apparent.
Figure 3:
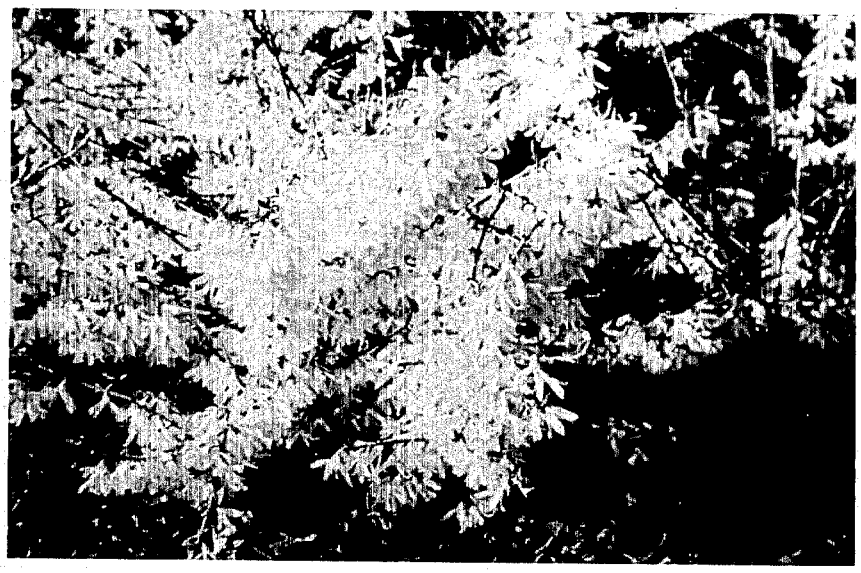
FIG. 3 illustrates a closer view of the attractive bright yellow flowers formed on a plant while growing outside in the landscape.
Figure 4:
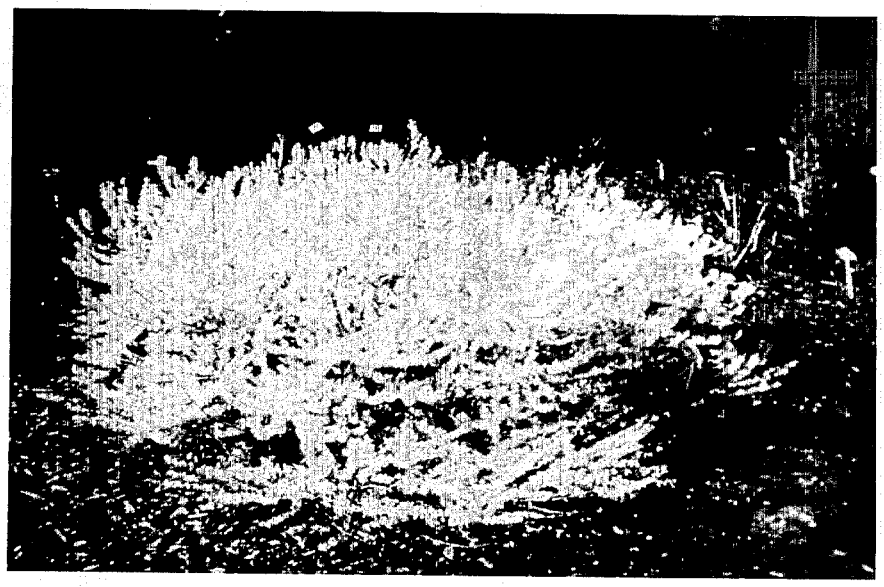
FIG. 4 illustrates the attractive low-spreading and compact growth habit of a five year-old plant while growing outside in the landscape during flowering.

The following description of the new variety was prepared following the observation of plants growing above the ground in containers at St. Barthelemy d'Anjou, France, and at West Grove, Pa., U.S.A. The chart used in the identification of the colors is the R.H.S. Colour of The Royal Horticultural Society, London, England.

Classification:

*Botanical.*—Forsytha cv. Courtasol.

Foliage:

*Type.*—Hardy, deciduous spreading shrub for garden decoration and general landscape use.

*Shape.*—Ovate lanceolate with an acute tip.

*Leaf margins.*—Dentate, and commonly exhibit approximately 23 dentations per leaf.

*Leaf length.*—Commonly approximately 8 cm.

*Leaf width.*—Commonly approximately 2 cm.

*Petiole.*—Commonly approximately 1.3 cm. in length, and commonly ranges on the upper side between Green Group 137C and Yellow-Green Group 144A in coloration.

*Leaf stems.*—Young stems. Approach Yellow-Green Group 144A in coloration. Mature stems. Yellow-Green Group 144A to 146B in coloration.

Young leaves.—Upper surface: Commonly range from Green Group 137C to Yellow-Green Group 146B in coloration. Under surface: Yellow-Green Group 146B in coloration.

*Mature leaves.*—Upper surface: Green Group 137B in coloration. Under surface: Yellow-Green Group 147A in coloration.

Branches:

*New growth.*—Appearance: The surface generally is smooth with some wide some wide ridges, and some lenticels are present. Color: Yellow-Green Group 144A.

*Mature wood.*—Appearance: The surface generally is smooth, and with some lenticels which tend to be more prominent than on the current growth. Color: Yellow-Green Group 146C to 146D.

Inflorescence:

*Time of blossoming.*—Early spring.

*Flower bearing.*—Commonly are present in clusters of 4 wherein the clusters are axillary, pedicelled and heterostylous.

*Calyx.*—Yellow Group 13B in coloration.

*Corolla lobes.*—Deeply four-lobed, veined on the interior surface, tend to be longer than the campanulate tube, and Yellow Group 13B in coloration.

*Stamens.*—Two stamens commonly are attached to the base of the corolla, the style is slender and possesses a two-lobed stigma, and the style commonly is approximately 1.5 to 2 mm in length. The flowers are currently brevistyled.

*Flower size.*—The overall length commonly is approximately 2.75 to 3 cm.

I claim:

1. A new and distinct variety of Forsythia, substantially as herein shown and described, characterized particularly as to novelty by the unique combination of:

(a) the exhibition of a distinctive low-growing, compact and spreading growth habit, and (b) the formation of a dense and abundant display of attractive bright yellow flowers that is influenced by the short internode lengths.

* * * * *